US005762072A

United States Patent [19]

Conlan et al.

[11] Patent Number: 5,762,072
[45] Date of Patent: Jun. 9, 1998

[54] COMPARATOR APPARATUS AND SYSTEM FOR ACTIVITY MONITORS

[76] Inventors: Robert W. Conlan, 1000 Stephen Dr., Niceville, Fla. 32578; Markham C. Godwin, 2006 Las Vegas Trail, Navarre, Fla. 32566

[21] Appl. No.: 450,345

[22] Filed: May 25, 1995

[51] Int. Cl.⁶ .................................................. A61B 5/103
[52] U.S. Cl. .............................. 128/782; 128/774; 607/19
[58] Field of Search .................................. 128/782, 670, 128/671, 690, 721, 774, 722, 687, 713, 714; 607/19

[56] References Cited

U.S. PATENT DOCUMENTS

| | | | |
|---|---|---|---|
| 3,797,010 | 3/1974 | Adler et al. | 128/782 |
| 4,428,378 | 1/1984 | Anderson et al. | 607/19 |
| 4,864,603 | 9/1989 | Battmann et al. | 379/106 |
| 4,888,589 | 12/1989 | Bowers | 341/153 |
| 5,008,940 | 4/1991 | Blum | 381/31 |
| 5,031,614 | 7/1991 | Alt | 607/19 |
| 5,197,489 | 3/1993 | Conlan | 128/782 |
| 5,273,041 | 12/1993 | Richards et al. | 128/653.2 |
| 5,283,579 | 2/1994 | Tasdighi et al. | 341/145 |
| 5,379,229 | 1/1995 | Parsons et al. | 364/478 |

*Primary Examiner*—Michael Buiz
*Assistant Examiner*—Patrick W. Rasche

[57] ABSTRACT

A comparator for comparing the operation of activity monitors of the type having internal sensors responsive to excitation forces in order to record the activity of a wearer, includes a housing having a test platform and a monitor-receiving test fixture for holding an activity monitor motionless during testing. The comparator further includes an electromagnet for applying an excitation force to the monitor, by converting a prerecorded digital signal, or waveform, into analog voltage signals which are applied to the electromagnet for testing the monitor. The monitor may be subjected to a variety of test patterns of activity.

20 Claims, 6 Drawing Sheets

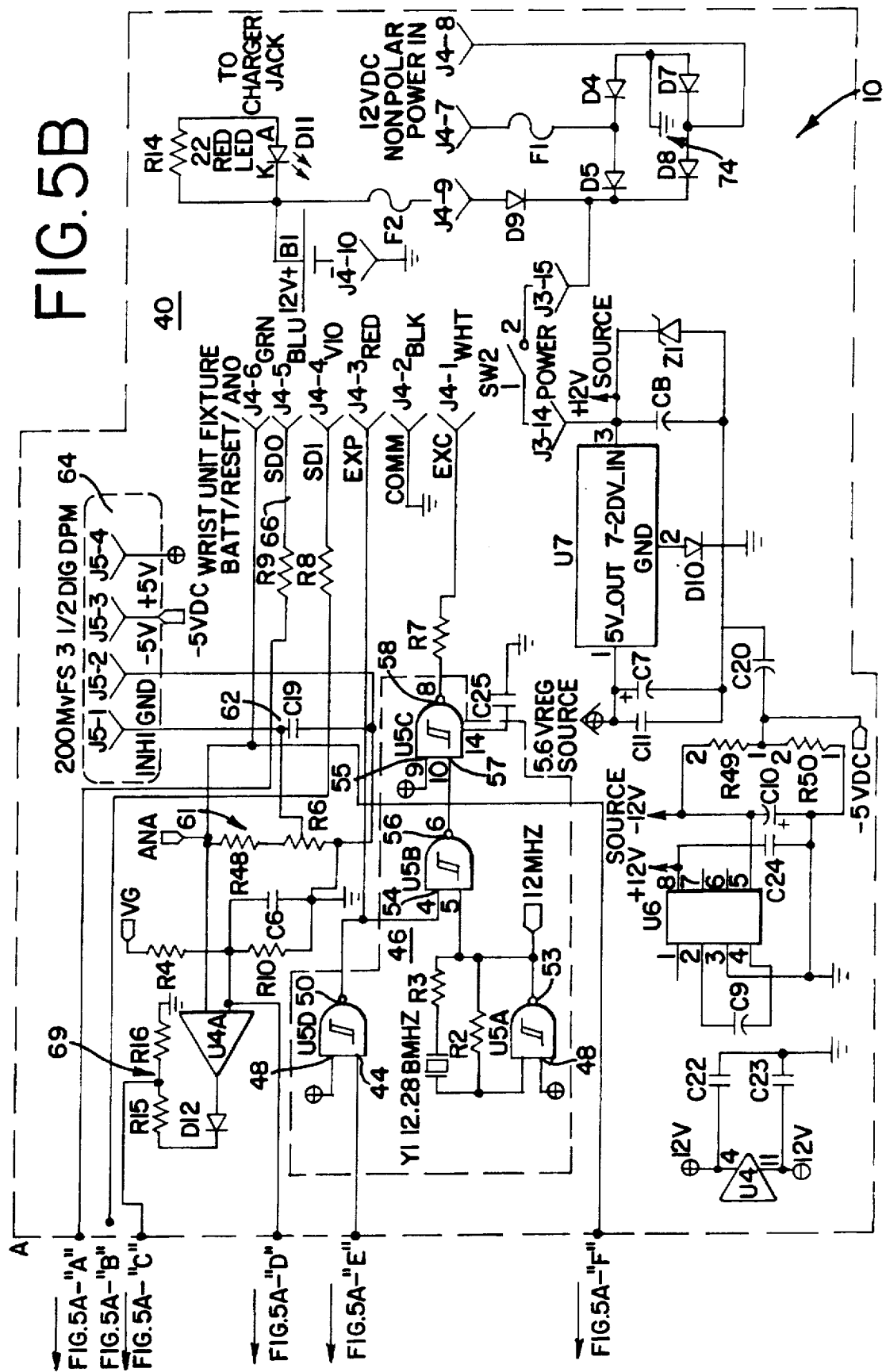

COMPARATOR APPARATUS AND SYSTEM FOR ACTIVITY MONITORS

BACKGROUND OF THE INVENTION

The present invention relates generally to activity monitors, such as actigraphs. More particularly, the invention relates to apparatus and methods by which the operation of such monitors may be recorded and compared against others to determine reliability characteristics thereof.

Activity monitors are known for observing and quantifying certain aspects of movement of a human without the attendant need and involvement of an observer. One such monitor is described in applicant's patent, U.S. Pat. No. 5,197,489, issued Mar. 30, 1993 for "Activity Monitoring Apparatus With Configurable Filters". The monitor disclosed in the '489 patent is described as an actigraph which independently records, on a simultaneous basis, certain levels of activity of its wearer, such as heart rate, respiration rate, muscle and skeletal movement and the like. These particular activities are of a very low frequency and are recorded by the monitor against time. The monitor records these activities by use of an internal, inertial sensor. The subject activities are recorded by the monitor and may subsequently be downloaded into an appropriate analysis device, such as a computer, where the data may be selectively analyzed and printed out. To obtain the data recorded by the monitor, the '489 patent describes an actigraph interface unit, or AIU, which receives the actigraph and provides an interface between the actigraph and a computer.

In the mass production of activity monitors, and particularly in the production of actigraphs disclosed in the '489 patent, it becomes desirable to effectively calibrate the monitors to detect and record the low frequency activities described above. Moreover, it is also desirable to determine the reliability of all the monitors in a particular manufactured lot of the monitors, that is, to determine if they all detect and record the same activity. One means of testing such activity monitors may involve mounting them in serial order on a pendulum in order to replicate the movement of a human. This type of testing involves serial testing of each monitor of a lot and then comparing the data recorded by each individual monitor to determine the efficacy and reliability of operation of the monitors within the tested lot. One obvious disadvantage to this type of reliability testing is that not only does it require a large amount of time and a special test facility, but it also involves the use of an apparatus to induce a physical movement into the monitor. When using such a physical apparatus, care must be taken in order to ensure exact placement of each monitor on the pendulum inasmuch as placement on the pendulum will affect the forces and movement the monitor will undergo.

A need therefore exists for a device for comparing the performance of activity monitors by uniformly exciting such monitors with a constant excitation signal which does not require a complex physical apparatus, such as a pendulum, and which easily records the operational data from a monitor.

Accordingly, it is a general object of the present invention to provide an improved apparatus, system and methods for exciting activity monitors in a manner which is easily reproducible and which may be used to compare the performance of any one activity monitor within a lot of monitors to the remainder of the lot.

Another object of the present invention is to provide a activity monitor comparator which is compact and which replicates ranges of human activity by non-physical means so that the performance of individual activity monitors may be analyzed against other such monitors.

Another object of the present invention is to provide an activity monitor comparator device in which the operational characteristics of activity monitors are stored.

Yet another object of the present invention is to provide an apparatus for activating activity monitors and comparing the data recorded thereby, wherein the apparatus includes a means for generating, and oscillating a magnetic field in response to a predetermined signal which causes an excitation of the activity monitor sensor, the magnetic field being capable of being generated at very low frequencies which replicate the frequencies of muscle and skeletal movement and/or heart and respiration rates.

Yet still another object of the present invention is to provide an activity monitor comparator apparatus which has interface capabilities for data exchange between an activity monitor and a host computer and which has an excitation circuit which electronically excites an activity monitor sensor in order to replicate human activity of a low frequency nature, the excitation being effected by a digital input which is converted to an analog signal.

SUMMARY OF THE INVENTION

The present invention is directed to an activity monitor comparator and methods by which the recording of activities may be induced in activity monitors in serial order in a plurality of activity monitors in which the monitors utilize an activity sensor of the accelerometer type which exhibits responsiveness to a magnetic field, so that the activity recorded in each such monitor may be accurately recorded and compared against each other.

In accordance with these and other objects, the present invention includes a housing for the comparator having an activity monitor engagement portion thereon which holds, the activity monitor motionless during testing. One preferred embodiment of the comparator includes a compact housing suitable for positioning upon a desk near a computer.

In particular, the comparator of the present invention includes a means for exciting the activity monitor sensor to replicate certain human or test activities, while the monitor is held motionless in a test fixture. A preferred excitation means is an electromagnet which receives a control signal in the form of an analog waveform generated by a digital-to-analog converter and which generates a magnetic field of a particular strength and at a particular frequency in order to replicate a range of human activity. This magnetic field operates to excite, or deflect, the activity monitor sensor during a test. After the excitation period or test completion, the comparator serves as an interface with a host computer so that the activity recorded by the activity monitor may be compared with the activity represented by the excitation of the comparator. In order to ensure accuracy in testing, a means for generating precise and controllable excitation waveforms is provided so that a variety of waveforms which replicate various levels of human activity may be used for testing by the comparator.

In the preferred embodiment, the comparator may utilize an address generator for generating the precise and reproducible excitation waveforms that are applied to a read-only memory (ROM). The ROM is in communication with a digital-to-analog converter which controls a power means which in turn feeds the electromagnet at a predetermined frequency so that the electromagnet generates a magnetic field in a pulsing manner to thereby excite the monitor in a manner virtually identical to the initial testing waveform.

The ROM is used to store patterns of activity in a manner so that they may be retrieved in an appropriate manner to supply an input to a converter. The activity pattern stored in the ROM is in binary format and is passed through a digital-to-analog converter to convert it into an analog voltage signal. The converter supplies this output to a power transistor which generates a current based upon the voltage signal supplied to it, which current is used to power the electromagnet. The ROM thereby provides a means by which specific activity patterns may be used to excite the activity monitor.

A redundant, isolated RS-232 data communication line is also preferably provided in the comparator on the communication side thereof, for isolation purposes. This isolates the host computer from the comparator during testing so that no DC coupling occurs between the computer and comparator.

BRIEF DESCRIPTION OF THE DRAWINGS

The features of the present invention which are believed to be novel are set forth in the appended claims. The invention, together with the further objects, features and advantages thereof, may be best understood by reference to the following description, taken in conjunction with the accompanying drawings, in the several figures of which like reference numerals refer to like elements, and in which:

DESCRIPTION OF THE PREFERRED EMBODIMENT

Figure 1:
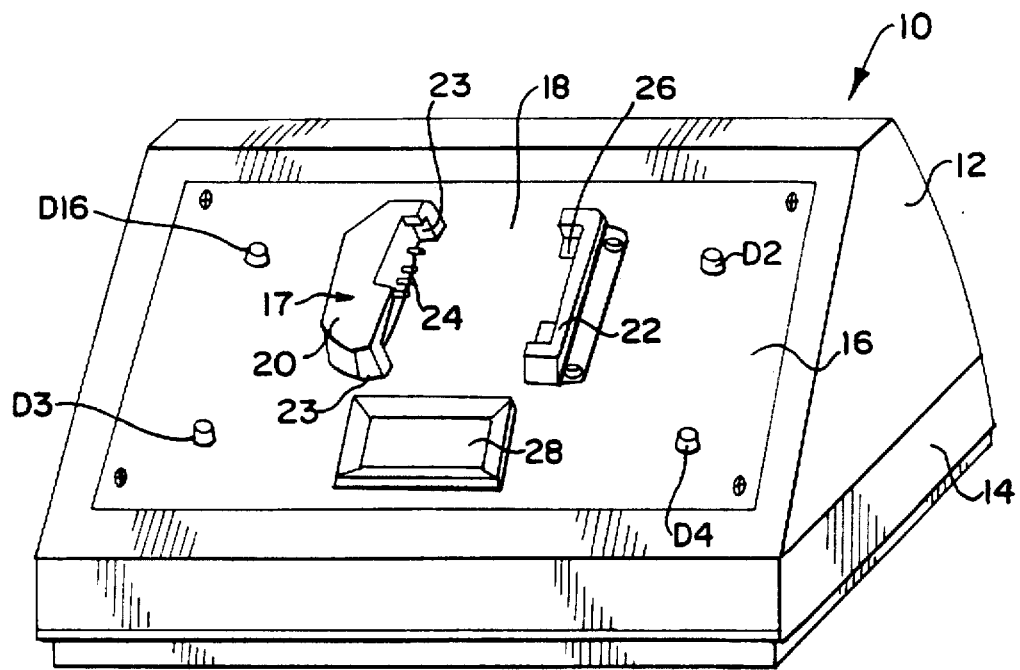
FIG. 1 is a perspective view of an activity monitor comparator constructed in accordance of the principles of the invention.

Referring to the Figures, and particularly to FIG. 1, an activity monitor comparator is illustrated generally at 10. The comparator 10 includes a housing 12 having a base 14 and a testing surface, or platform 16. The comparator 10 functions in conjunction with an activity monitor, or actigraph 100, such as that disclosed and claimed in my prior U.S. Pat. No. 5,197,489, the disclosure of which is herein incorporated by reference.

Figure 3:
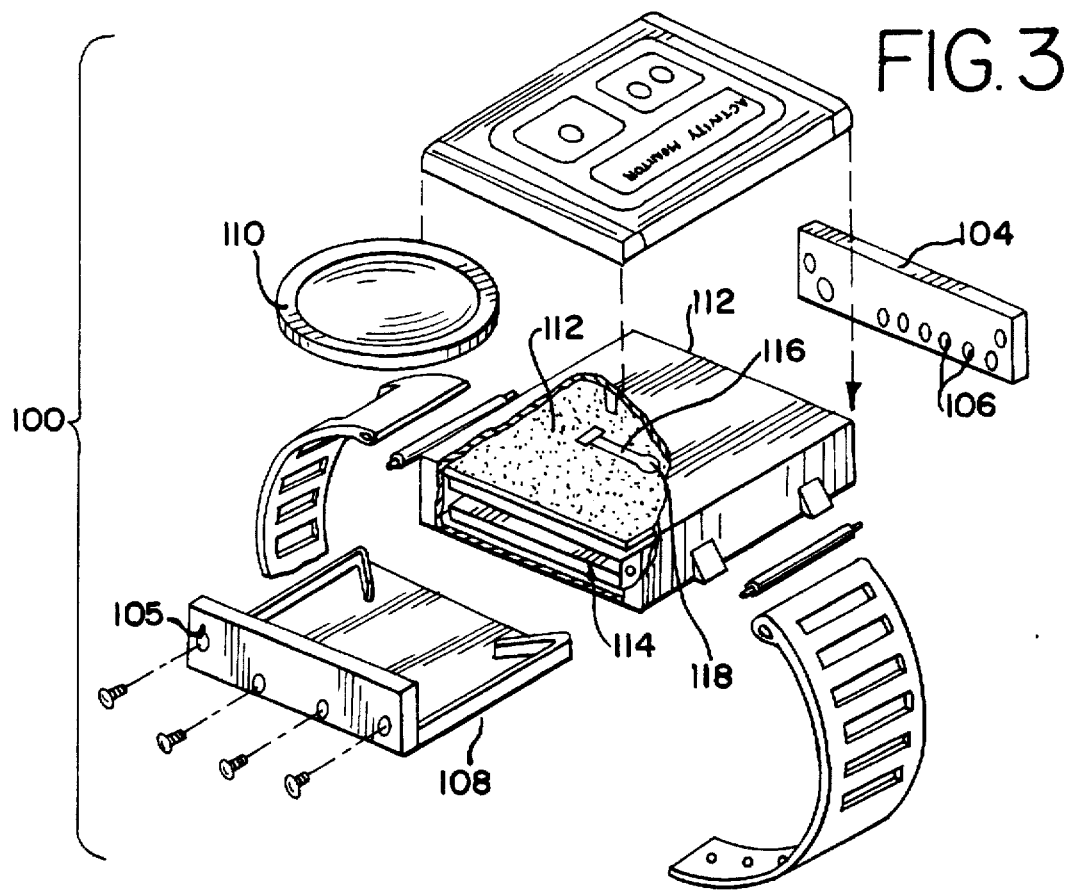
FIG. 3 is an exploded view of an activity monitor suitable for use in the present invention.

The actigraph 100 illustrated, and that described in the aforesaid U.S. Pat. No. 5,197,489 is worn on the wrist of a user and is seen in FIG. 3 to include a housing 102 having a series of side panels, one of which 104 includes a plurality of electrical contacts 106 adapted for engagement with opposing terminals 24 of the comparator 10. The lower portion of the activity monitor housing 102 may include a sliding-tray assembly 108 in which a battery 110 may be positioned for insertion into the housing 102 in order to supply power to the internal circuitry thereof.

A series of internal circuit boards 112, 114 are supported within the monitor housing 102 and provide substrates for the mounting of various circuit components of the monitor. As described in said U.S. Pat. No. 5,197,489, the monitor 100 may include an internal motion sensor, illustrated as a cantilevered piezoelectric bimorph beam 116. The beam may also include a metal disk 118 disposed at its free end, which disk is referred to as a proof mass. This motion sensor senses motion and activity of the wearer, such as muscle and skeletal movement, heart rate, breathing rate and the like. These types of human motions and activities occur at low frequencies, typically ranging from between about 0.1 Hz to about 10 Hz, with most human activities of interest having low frequencies in a range between about 0.2 Hz to 0.3 Hz. The electrical output of this sensor is amplified, filtered and digitized in several possible ways, and the resulting digital data is stored by a microcontroller in a random-access memory (RAM) of the activity monitor 10.

This activity data may be downloaded from the monitor 10 and typically requires the use of an interface unit which provides a data transfer connection between the activity monitor microprocessor (not shown) and a host computer 30. The comparator 10 of the present invention may serve as such an interface unit and importantly represents an improvement over a conventional interface unit in that the comparator 10 permits analysis, or comparison, of the sensor response of two or more activity monitors by providing a signal to the activity monitor for test purposes.

Figure 4:
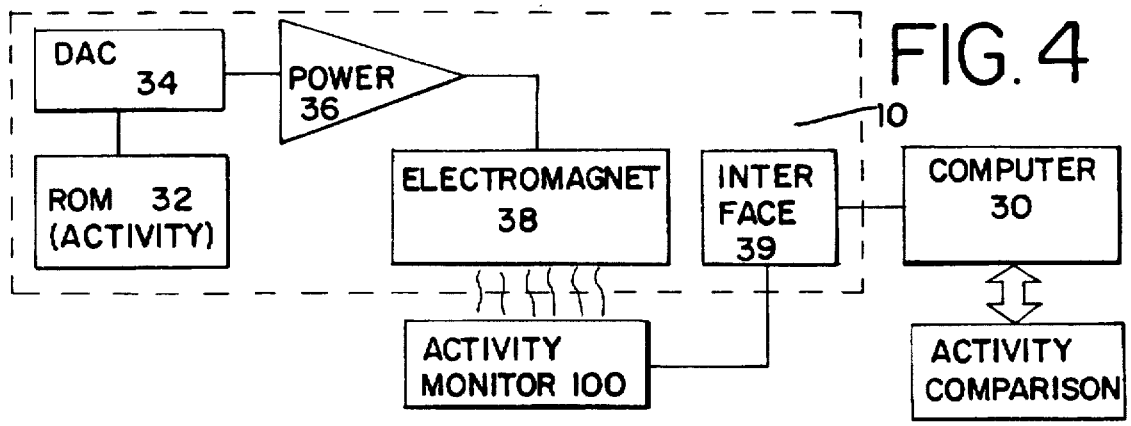
FIG. 4 is a functional block diagram showing the principal components of the activity monitor comparator system shown in FIG. 2.

When used as part of an overall test system as illustrated in FIG. 4, the comparator 10 performs two functions. It provides a means for generating a predetermined excitation to the activity monitor 100 and also provides a means for communicating with a host computer 30. The excitation of the activity monitor 100 is accomplished by retrieving a previously stored activity pattern from a ROM 32. The digital activity pattern is converted to an analog voltage by way of a converter 34 which is linked to a power module 36. Various voltages may then be applied to the comparator electromagnet 38 in order to excite the activity monitor 100. During or after excitation, the pattern recorded by the monitor may be communicated to the host computer 30 by way of an interface 39 which permits data exchange between the comparator 10, the activity monitor 100 and the host computer 30.

Generally, the comparator 10 requires certain circuitry in order to permit it to properly interface with a host computer and perform its intended communication functions. First of all, a voltage shift should be provided so that the serial communication signals of the activity monitor 100 are compatible with the RS-232 communication signal level of the host computer 30 used for comparison purposes. Secondly, an accelerated clock frequency, or rate, such as 12.288 Mhz, should be supplied to the activity monitor 100 by the comparator 10 to allow data transfer at a fast rate to the host computer 30. Thirdly, an external voltage source should also be provided to the comparator 10 to the activity monitor 100 that the data transfer may be effected at the accelerated clock rate. Fourth, the comparator 10 should preferably include a means for measuring the activity monitor's internal voltage in order to permit the battery condition of the activity monitor 100 to be assessed and displayed. Fifth, the comparator 10 should still further include a provision for resetting the activity monitor 100.

In order to provide a secure testing platform for the activity monitor 100 as illustrated in FIG. 1 and in order to importantly hold the monitor motionless during testing, the comparator 10 includes a housing 12 having a monitor-receiving test fixture 17 having a slot 18 defined between two opposing engagement and retention members, illustrated as elongated walls 20, 22 which rise above the testing surface 17 of the comparator 10. Preferably, the housing 12 is formed from a durable non-magnetic material, such as aluminum or the like. The slot 18 is intended to receive a single activity monitor therein and reliably hold it motionless to eliminate any outside movement interference. Appropriately, the engagement walls 20, 22 may include recesses, or notches 23, into which at least part of the activity monitor 100 is preferably held motionless.

One engagement wall 20 includes a plurality of electrical terminals 24 extending therefrom and aligned with a like number of electrical contacts 106 formed on the activity monitor 100. The other engagement wall 22 of the comparator test fixture 16 includes one or more spring contacts 26 which serve to engage the other side panel 105 of the monitor 100 and retain the activity monitor 100 in place within the test fixture 16 and notches 23 thereof. A means for displaying the internal voltage of the activity monitor, shown as an LCD panel 28, is positioned on the comparator test surface 16 in proximity to the test fixture thereof. Although the comparator 10 is illustrated in the Figures and as described hereinafter as accommodating only a single activity monitor 100, it will be understood that the present invention also encompasses a comparator apparatus which may accommodate a series, or gang, of activity monitors upon the test platform.

In addition to the five circuits generally mentioned above, the comparator 10 also preferably includes a means for automatically switching between two different modes of operation of the comparator 10 and a means for automatically detecting the presence of an activity monitor in the testing fixture.

Importantly, the comparator 10 further includes a means for supplying a predetermined test signal to the activity monitor in place within the test fixture of the comparator 10. This test signal preferably may be stored in a digital form in an internal memory, preferably a ROM 32.

Data retrieved from the ROM are processed by a digital-to-analog converter 34 (DAC) in order to present an analog voltage signal which may be amplified and subsequently applied to the internal electromagnet 38 to create a magnetic field in proximity to the activity monitor 100, when mounted on the comparator 10. This magnetic field acts on the activity monitor sensor, typically exciting the proof-mass 118 on the end of the piezoelectric beam 116.

The activity monitor, in normal operation, detects motion of the wearer by way of measuring the acceleration of the beam (and the user) and electronically converts it into a signal voltage which is stored in a RAM of the activity monitor. The proof-mass 118 used in the activity monitor of the above-mentioned '489 patent increases the sensitivity of the piezoelectric beam 116 to acceleration. The magnetic field generated by the comparator 10 induces movement of the proof-mass 118 in relation to the strength of the magnetic field.

Interface Aspects of the Comparator

Figure 5A:
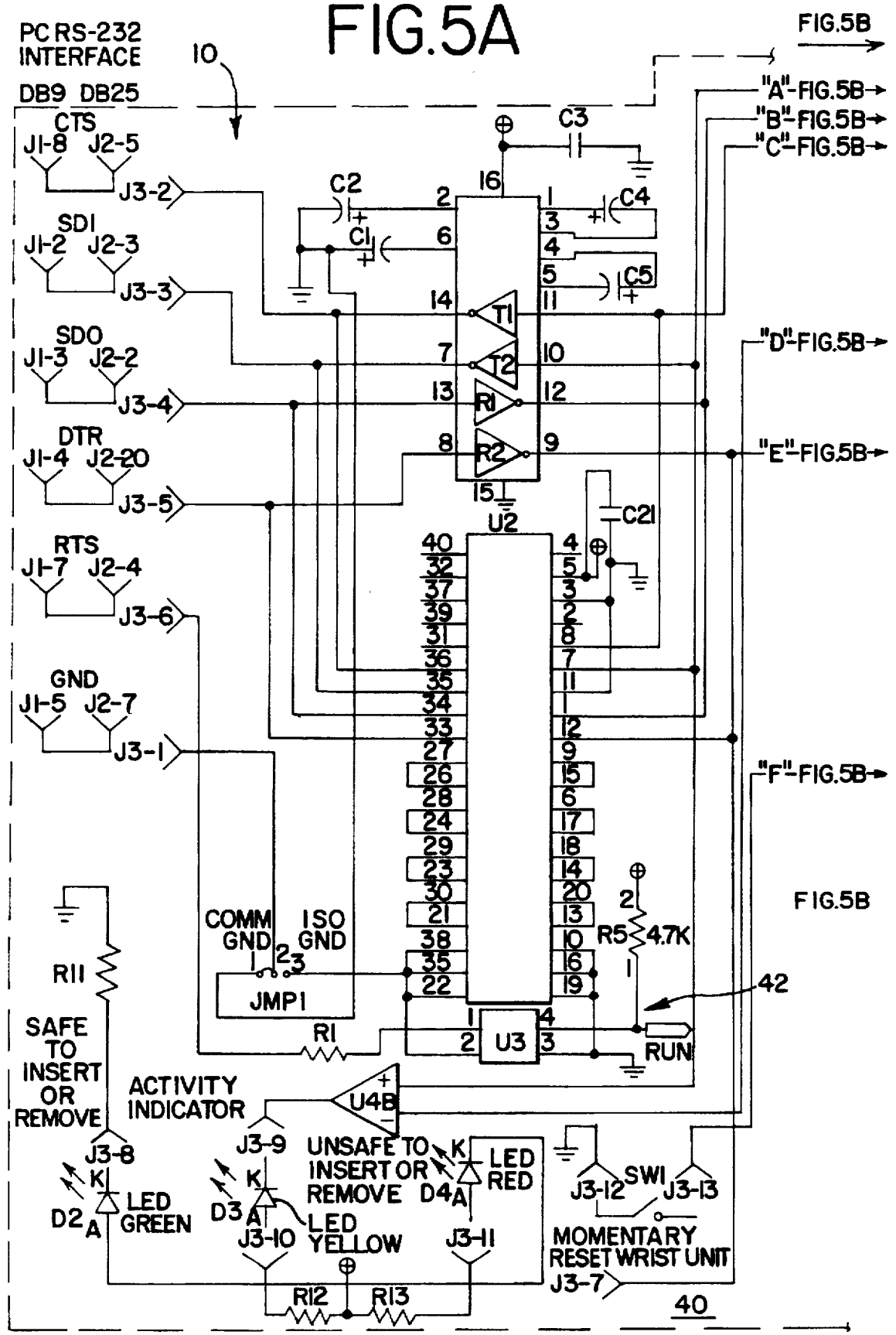
FIGS. 5A & B, when combined along line A—A are a circuit diagram of the circuitry utilized in a preferred embodiment of a comparator constructed in accordance with the invention.

As mentioned above, the comparator 10 includes an interface aspect which provides a means for establishing communication between the monitor 100 and the host computer 30. FIGS. 5A & 5B, combined, are a schematic diagram of the comparator 10 which illustrate the details of the RS-232 communication level shifting which is performed by the comparator 10. The comparator 10 includes means for adapting the serial-port voltages which the activity monitor emits to the requirements of RS-232 standards for serial port data communications.

In conventional digital circuits, logical 0 is usually designated by a signal voltage level of about 0 volts, while logical 1 is designated by a signal voltage level +5 volts, typically equivalent to the power supply voltage. However, an RS-232 data transmitter typically requires a voltage between −5 volts and −15 volts to designate a logical 1, indicating that RS-232 signals have a reverse polarity of standard digital logic signals and generally occur at higher voltages. Most digital circuits are powered by a single 5-volt power supply which creates difficulty in meeting the RS-232 signal requirements. The RS-232 data communication standard also requires positive and negative voltages and the positive voltages must typically be greater than 5 volts to allow for any voltage drop which may occur in the line driver output transistors. The comparator 10 effectively shifts the voltage level associated with the RS-232 data transfer.

As illustrated in FIG. 5, the comparator 10 includes an IC chip U1 which provides two RS-232 line drivers and two RS-232 line receivers shown as inverting amplifiers, T1, T2, R1 and R2 because of the reverse polarity of RS-232 signals. A suitable chip for this application is a MAX 232, manufactured by Maxim. The chip U1 requires a +5 volt power supply and the IC includes a voltage doubler circuit in order to develop an appropriate +10 volt power source. The chip U1 also includes an inverting voltage doubler to develop a −10 volt power source from its initial power source of +10 volts. Two external capacitors C1, C2,C4 & C5 are illustrated as applied to each voltage doubler. A bypass capacitor C3 may also be provided for chip U1, which is an opto-isolator.

In order to provide opto-isolated RS-232 communications, another chip, U2 a 40-pin DIP (Dual inline pin) chip may be used in place of chip U1. A suitable chip for this parallel application is a MAX 252, a transformer and opto-isolated RS-232 line transceiver, also manufactured by Maxim, which is a multi-component module in a 40 pin DIP package which provides transformer and opto-isolated RS-232 data communications. The chip U2 may include a noise bypass capacitor C21. The RS-232 side of the chip U2 is powered by an internal transformer so that the RS-232 line side of the chip U2 is electrically isolated relative to the TTL side. The module chip U2 effectively breaks ground loops and provides a higher degree of noise immunity to devices utilizing an RS-232 line for communication. This isolation circuitry is provided to ensure that the comparator 10 will function effectively with all host computers.

Only one of the two chips U1, U2 need be installed in a particular comparator, and a jumper JMP1 is configured for the particular interface based upon the chip installed. When used with an opto-isolated chip, such as the module chip U2, the jumper JMP1 should be in the "ISO GND" position and for use with a non-isolated chip, such as the MAX 232 chip U1, it should be in the "COMM GND" position. Connector pins J3-1 through J3-6 serve to connect the RS-232 interface to the printed circuit board 40 of the comparator 10, while another connector J1, which is externally mounted to the comparator housing 12 provides the means of interconnecting the comparator 10 and the host computer 30. The connector J1 may take the form of a 9-pin D-shell connector.

Another connector J4, preferably takes the form of a 15-pin connector and six of the pins are connected to the activity monitor test fixture 17 on the comparator test surface 16. One of these pins J4-5, designated SDO for "Serial Data Output", receives serial data from the activity monitor 100 in place within the comparator test fixture 17. A resistor R9 is provided as a current-limiter to prevent any damage to the activity monitor being tested. Once voltage level shifting is accomplished by either chips U1 or U2, the signal from this line travels to pin J3-4, designated SDI for "Serial Data Input" to thereby send serial data from the activity monitor 100 to the host computer 30. Pin J3-4, designated SDO for "Serial Data Output", receives serial data from the host computer 30. Once voltage level shifting has been accomplished by either chip U1 or U2, this signal travels to pin J4-4, designated SDI for "Serial Data Input" on the monitor side of the interface and delivers serial data to the activity monitor 100, also through a current-limiting resistor R8.

A single opto-isolator U3, such as a Digikey P52702-1NEC-ND, may be utilized to couple the RS-232 signal designated RTS, for "Request to Send", which is used to control playback of the ROM waveform from connector pin J3-6 to the waveform generator circuit 60. A current-limiting resistor R1 is provided to limit current through an internal LED of chip U3. A voltage divider 42 is formed by resistor R5 and the internal transistor of chip U3.

Inasmuch as RS-232 signals are of a negative-logic type in that when an RS-232 signal (after having been converted to TTL levels) is a logical one in about +5 volts, the signal is negated. However, when the RS232/TTL line is a logical 0 and has a value of about 0 volts, the signal is asserted. Thus, when the signal from RTS is asserted at about +10 volts on the RS-232 line side, the internal LED of the opto-isolator U3, conducts, and its light enables the photo-transistor to become conductive. The photo-transistor pulls a signal labeled "RUN" low, thereby enabling the digital ROM playback.

As an interface, the comparator 10 also applies an accelerated clock rate, about 12.288 MHz, to the activity monitor 100 in the test fixture 17 when the comparator 10 is put in a communication or "COMM" mode by the host computer 30. The host computer 30 automatically switches the comparator 10 between the "COMM mode" and the "INSERT/REMOVE" mode by using the RS-232 line designated DTR, for "Data Terminal Ready", which arrives at pin J3-5. This signal line is level shifted by either chip U1 or U2 and is presented at pin 44, to a quadruple Schmitt-triggering NAND gate package 46, which contains four NAND gates U5A, U5B, U5C & U5D. A suitable such Schmitt trigger is a MC74AC132M quad NAND gate available from Motorola.

One input pin 48 of NAND gate U5D is tied to the +5 volt power supply, making the gate U5D an inverter. The signal on the output pin 50 of U5D is therefore high when the host computer 30 asserts DTR to place the comparator 10 into the "COMM mode". At the same time, gate U5A operates as an oscillator and input pin 52 of this gate is tied high which causes the gate U5A to behave as an inverter. A resistor R2 renders the gate U5A somewhat unstable while crystal Y1 sets the resonant frequency of the circuit, while another resistor R3 limits the signal strength. The digital signal on output pin 53 of the oscillator gate U5A is labeled "12 Mhz" in FIG. 5.

A third gate U5B of the Schmitt trigger package 46 is interconnected to the oscillator U5A and gates the oscillator signal on and off in accordance with the DTR signal received from the host computer 30. When DTR is asserted, input pin 54 of gate U5B is pulled high, thereby permitting the 12.288 Mhz signal to reach the output of the gate. When DTR is negated, input pin 54 of the gate U5B is pulled low, forcing the gate output to go high.

A fourth gate U5C of the package also functions as a simple inverter because its input pin 55 is tied high. The gated oscillator signal from the output 56 of gate U5B is applied to input pin 57 of the fourth gate U5C. This gate outputs a 12.288 Mhz signal when DTR is asserted, and outputs a logic low of about 0 volts when DTR is negated. The output of this gate U5C is current-limited by resistor R7 to protect the activity monitor 100 of possible overload and travels to the monitor by way of pin J4-1. A noise decoupling capacitor C25 may be provided for the Schmitt trigger package 46.

An additional characteristic of the interface aspect of the comparator is the application of external power to the activity monitor 100 when the comparator 10 is in the "COMM mode". This function is performed by NAND gate U5D where the output of gate U5D is a logical high of about +5 volts when the host computer 30 asserts DTR. When the computer negates DTR, this gate output falls low to about 0 volts. The Schmitt trigger package 46 can supply the entire current requirements of the activity monitor 100 using the output of one gate U5D, which travels to the monitor 100 by way of pin J4-3.

The comparator 10, in another interface aspect, further measures the internal voltage of the activity monitor 100 which permits the battery condition of the activity monitor 100 to be assessed by the operator. This voltage is displayed on the comparator LCD panel 28 which is designed to operate from a 9-volt battery. The meter is powered from the +5 volt power supply and an unregulated −5 volt power source. The LCD panel 28 has negative and positive input terminals, respectively "INLO" and "INHI". The voltage is displayed between these two terminals on the LCD 28. The voltage difference between INHI and INLO may range from between −200 millivolts to +200 millivolts. The voltage of the activity monitor 100 arrives at pin J4-6. This voltage is divided by a factor of 100 in a voltage divider 61 consisting of resistor R48 and potentiometer P6.

A filter 62, in the form of capacitor C19, filters noise from the signal going to the LCD meter to give more accurate readings. After dividing and filtering, the voltage is sent to the meter INHI input by way of pin J5-1. Pin J5-2 sends a circuit ground to the meter INLO input. Pin J5-3 sends an unregulated −5 volts to the meter while pin J5-4 sends +5 volts power to the meter. These 4 pins are preferably encompassed in a suitable connector, such as a 6-pin connector, at 64, on the comparator circuit board 40.

Another interface function of the comparator 10 is a manual reset of the activity monitor 100 by way of a pushbutton switch SW1. The switch SW1 is connected to the PC board at pins J3-12 & J3-13. When pressed, a circuit ground is connected to the activity monitor "Reset" pin through pin J4-6 and the activity monitor microcontroller is held in reset while switch SW1 is depressed. When the switch is released, the activity monitor resumes collecting data. This reset function ensures that their microcontroller starts properly when power is applied to the circuit.

As part of this circuit, pin J4-6 on the comparator circuit board 40 is interconnected to pin on the activity monitor designated "BATT/RESET/ANO". This pin passes the activity monitor's internal voltage for monitoring, permits resetting of the activity monitor and monitors the output of the analog signal-processing circuitry of the monitor. The voltage monitoring and reset functions are effective at the pin because of the reset circuit design of the activity monitor 100 which includes a resistor connecting the positive power supply with the microcontroller reset pin. A capacitor in the activity monitor connects the reset pin the circuit ground such that when power has been absent, the capacitor discharges. When power is first applied the reset is held low for a short time. The activity monitor's external "BATT-RESET" pin connects to the microcontroller reset pin. When the comparator reset button is pressed, the microcontroller is reset. The positive power supply to the activity monitor may be measured through this pin by way of a pull-up resistor.

Additionally, with suitably equipped activity monitors, the comparator may monitor the output of the monitor analog signal-processing circuitry. This will occur in activity monitors which include an analog switch chip which allows switching of a pin from the reset 15 circuit to an analog-output circuit under control of the monitor's microcontroller.

The comparator 10 still further includes an automatic switching of the interface between the "COMM" and "INSERT/REMOVE" modes. The RS-232 signal designated DTR does the switching by means of the host computer 30. This DTR signal arrives on pin J3-5 and is level shifted by either chip U1 or U2 and then applied to one input 44 of NAND gate U5D. Gate U5D inverts the signal and supplies it, as external power, to the activity monitor 100. When DTR is asserted, external power is applied and when DTR is negated, external power is turned off. The output from gate U5D also turns on and off the external clockrate controlled by gate U5B. When DTR is asserted in the output of gate U5D is high, a 12.288 MHz clock signal from gate U5A is allowed through gate U5B. The signal proceeds through gate U5C and resistor R7 to pin J4-1. When DTR is negated, the output from gate U5B is high, and the output from gate U5C is low.

Yet still another characteristic of the interface function of the comparator 10 is the automatic detection of the presence of an activity monitor 100 in the test fixture 16. This detection is done by way of the activity monitor "BATT-RESET" pin which is normally at the activity monitor internal voltage as described above. This voltage arrives by way of pin J4-6 and travels to op-amp U4A as an inverting input. The other input of op-amp U4A, is a non-inverting input and is supplied a 0.6 volt reference voltage, which is developed by a voltage divider 66 which includes resistors R4 and R10. The divided reference voltage is obtained from a reference source of +1.2 volts. A capacitor C6 is provided to keep this voltage steady.

The op-amp U4A functions as a comparator. If an activity monitor is present in the test fixture 17, the voltage arriving on the "BATT-RESET" pin will be higher than 0.6 volts and the U4A comparator output will swing to about −12 volts. If no activity monitor is present in the receptacle, the voltage arriving at the "BATT-RESET" pin will be about 0 and the output will be about +12 volts. A diode D12 and resistors R15 and R16 condition the output of the comparator so that it is compatible with TTL inputs. The diode D12 blocks −12 volts from the comparator to supply about 0 volts to the TTL input. The two resistors R15 & R16 cooperate to act as a voltage divider 69 and a current-limiter reducing the +12 voltage down to about +6 volts. This signal is level shifted by either chip U1 or U2 and sent out on pin J3-2 as the RS232 signal designated CTS, for "Clear To Send". The host computer 30 reads this signal to determine if an activity monitor 100 is present in the test fixture 16 of the comparator 10.

Signal Generating Aspects of the Comparator

Figure 6:
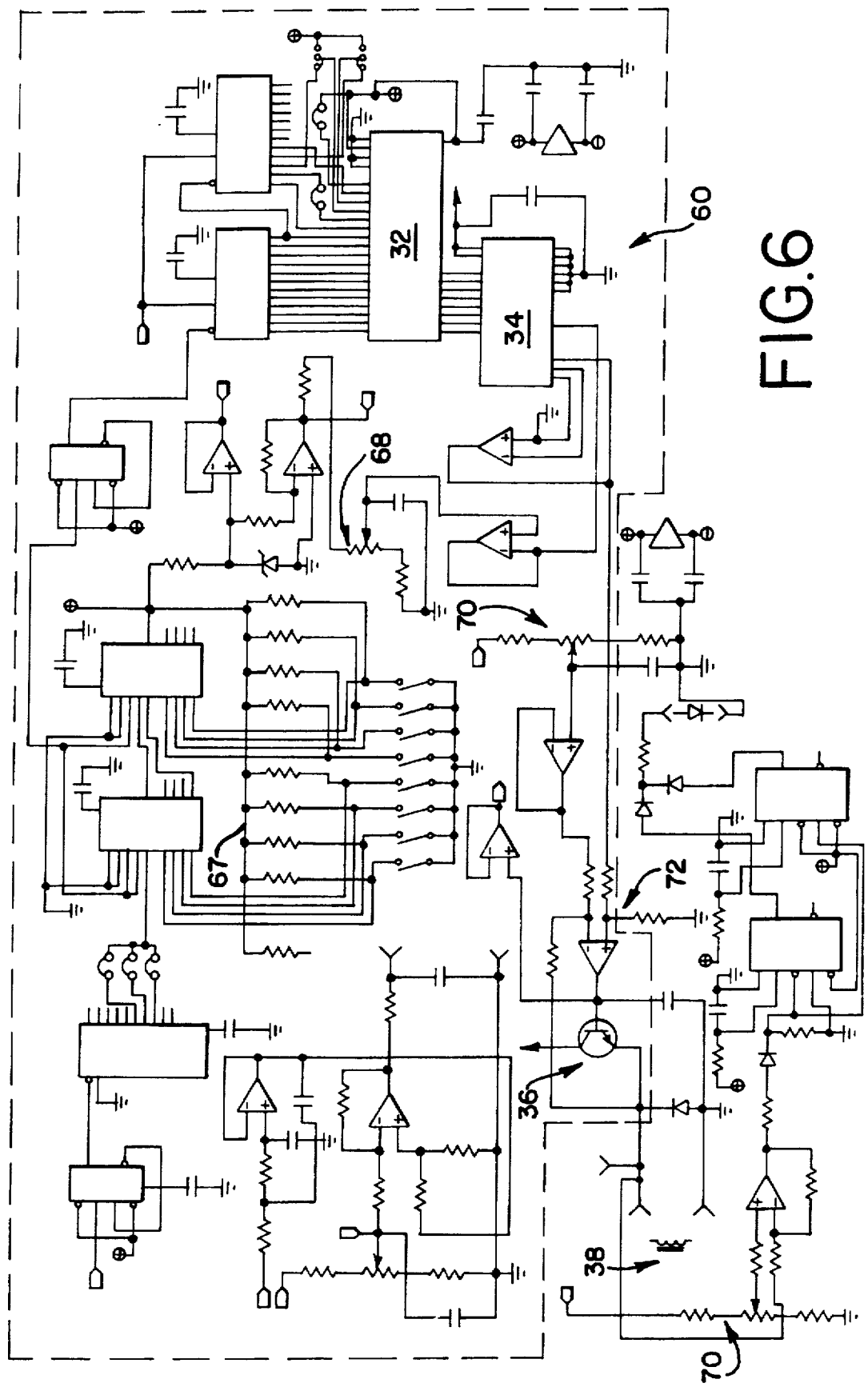
FIG. 6 is a circuit diagram of the circuitry utilized in a preferred embodiment of a waveform generator used in the comparator of FIGS. 1 and 4.

Turning now to FIG. 6, the signal generator portion of the comparator 10 is illustrated schematically. The signal generating aspect of the comparator 10 may be considered as having three subsystems or circuits: a frequency divider, a ROM playback and a digital to analog conversion.

Considering now the frequency division subaspect of the signal generator, the 12.288 MHz signal received from the oscillator U5A described above, is divided by two by a flip flop U11B, such as an M74HC74B1R available from SGS. Capacitor C30 serves as a bypass capacitor for the flip flop U11B. The resulting 6.144 Mhz signal is supplied to a multi-stage binary divider U8 which supplies a series of signals related in frequency by powers of 2. Three of these signals are supplied to jumpers JMP2, JMP3 and JMP4. Only one of these jumpers should be bridged in operation, so that a predetermined frequency of 12 Khz, 6 Khz or 1.5 Khz may be obtained.

The selected frequency is then supplied to the two cascaded presettable binary down counter chips U9, U10, such as CD4526BCN available from Digikey, which count downward from the binary value supplied on their program pins. When their count reaches 0, the counters U9, U10 reset themselves to that same binary value. These counter chips therefore produce a reset pulse every N counts, where N is the binary value supplied on the chip's preset inputs. An SIP resistor pack 67 is provided with resistors R19–26 & R62 and cooperate together with DIP switch S1 to supply an 8-bit binary number to a cascaded counter circuit. The number used on this switch with acceptable results have been $4B in hexadecimal, or %0100 1011 in binary, or 75 in decimal to yield an output frequency of 160 Hz. The pulses from this counter stage are used to toggle flip flop U11A. This action divides the pulse frequency by 2, to form of a 50% duty-cycle square wave. The square wave is the sampling rate in samples per second (SPS).

A ROM 32 is provided for reception and recall of particular patterns of activities with either predetermined or varying frequencies. The sampling clock described above is supplied to an address generator 60 which includes 2 cascaded binary up-counters U12, U13. The reset inputs of these two counters U12, U13 are controlled by the signal designated "RUN" which comes from the discrete opto-isolator U3 (FIG. 5) as described hereinabove. When the "RUN" signal is high, RTS is negated, and the counters are held in reset and have an output address of 0. When the "RUN" signal is low, RTS is asserted, and the counters U12, U13 are allowed to count. Capacitors C34 and C35 may be used as bypass capacitors for the counters.

The address output of the two counters U12, U13, is connected to ROM chip U14 (indicated as 32 in FIG. 6), such as a 27C512-12 EPROM available from Digikey. The ROM chip used may be in any of 8 k, 16 k, 32 k, 64 k or 128 k byte capacities. Four jumpers are required to correctly configure the ROM U14 based on its capacity. The first jumper, JMP8 connects the address line A13 to the ROM socket. When an 8k byte ROM is used, this jumper is absent. When any other capacity ROM is used, jumper JMP8 must be in place. The second jumper JMP6, controls the address line A14. For ROM chips 16 k bytes, or smaller, this jumper must be in the +5 volt position. For larger ROM, it must be in the signal position. A third jumper JMP7 controls A15 and must be in the +5 volt position for ROM chips of 32 k bytes, or smaller capacity. For larger ROM's, it must be in the signal position. Address line A16 connects to a pin on the 32 pin socket for use with a larger 32-pin 128 k byte ROM chip.

Smaller ROMS use a 28-pin package which will not contact pins 1, 2, 31 or 32 of the socket. On the smaller ROM chips, power is supplied via socket pin 30 but not with respect to the larger 128 k byte ROM chip. Accordingly, a fourth jumper JMP8 must be used for most ROM chips, but is not installed for 128 k byte ROM's. Capacitor C36 is a chip bypassing capacitor. In the configuration shown in FIG. 6, a 64 k byte ROM is used and therefore jumpers JMP8 and JMP5 are installed and jumpers JMP6 and JMP7 occupy their signal positions. The ROM chip's output lines are enabled at all time. Therefore, as the address supplied to the ROM advances, sequential bytes of data are output on the ROM data lines. The size of the ROM will vary depending upon the length of testing and the playback sample rate required for a particular type of activity pattern. The size of this memory may be easily included within the range of 8 k bytes to 128 k bytes. For example, 64 k of ROM memory will yield a signal duration of about 13 minutes, while 128 k of ROM memory will yield a signal duration of about 26 minutes. The comparator 10 will "wraparound" and play the same segment over and over unless commanded otherwise. The available once around runtime of the stored activity signal is approximately about 1 minute, 37 seconds for each 8 k of ROM memory. When using a ROM with a capacity of 64 k bytes, a clock rate of 80 samples per second (SPS) gives desirable results.

In order to effectively operate the electromagnet 38 to excite a monitor 100 in the test fixture 17, the data output from the ROM chip is delivered to the data input pins of an 8-byte DAC U15, which produces an analog voltage which is proportional to the binary number supplied to its input. In this regard, the DAC U15 requires a reference voltage to set the scale of its output. This reference voltage is developed by a voltage divider 68 which includes resistors R27, R29 and potentiometer R28. The potentiometer allows adjustment of the AC signal strength of the system. The voltage divider is connected to a source of regulated −5 volts and to a circuit ground. A capacitor C12 may be provided to reduce noise on the reference signal. An op-amp U4D, such as a LM324M-ND by Digikey, acts as a unity-gain voltage follower in order to buffer the reference voltage signal before it is supplied to the DAC U15. Another op-amp U4C conditions the output out of the DAC U4D.

A second voltage divider 70 includes resistors R34, R35 and potentiometer R36 produces a DC offset voltage which is added to the signal being output from the DAC U15. The potentiometer R36 allows adjustment of the DC level of the system. The voltage divider 70 is connected to a source of regulated −5 volts. A capacitor C35 reduces noise on this voltage and op-amp U16B acts as a unity-gain voltage follower to buffer the signal.

The AC signal from the DAC U15 and the DC signal from the voltage divider circuit 70 are brought together in op-amp U16A. The current source and capability of this op-amp is boosted by a transistor Q1, such as a TIP41A from Hamilton-Avnet, and feedback occurring from the emitter thereof allows op-amp U16A to adjust the transistor drive. The combined circuit forms a high-sourcing-current op-amp. A capacitor C15 eliminates any tendency of the system to self-oscillate. A diode D13 is provided as kickback suppression diode, to protective the transistor and op-amp from high voltage transients.

A coil L1 serves as the comparator's electromagnet 38. It is preferably embedded within a special steel housing consisting of a circular steel outer shell with an inner solid steel cylindrical mandrel 80 about which the coil wires 82 are wound and so positioned underneath the comparator test platform 16 proximate to the test fixture slot 18 in order to stimulate the proof-mass 118 of the activity monitor 100.

Figure 7:
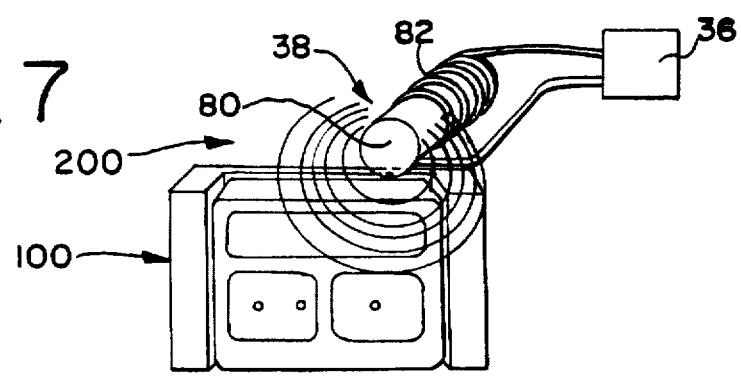
FIG. 7 is a conceptual diagram illustrating the magnetic field generating aspect of the present invention.

This is illustrated in FIG. 7, which indicates how the magnetic field 200 extends away from the pole and how the magnetic flux lines contact the monitor 100.

The electromagnet L1 is connected to the comparator circuit board 40 by way of pins J4-11 and J4-12 and forms the load of transistor Q1. The gain of the op-amp/transistor system is set by two resistors R30 and R33. The gain of the inverting input, through which the DC offset signal voltage arrives, is unity. The gain of the non-inverting input, through which the AC signals arrives, is 2. However, the AC signal is divided by two in the voltage divider 72 of R31 and R32 such that the total path gain from the DAC to the electromagnet is equal to 1. The output of op-amp U16A is buffered by op-amp U18D configured as a unity-gain voltage follower, and is available at a test point on the comparator circuit board 40. A copy of the signal to the electromagnet is provided on pin J4-15 for monitoring purposes. This signal at the electromagnet L1 is adjusted to approximately 2 volts DC and +/−500 millivolt AC.

The comparator 10 may also include a plurality of light-emitting diodes (LED's) mounted on its test surface 16 to provide visual indications of certain comparator functions. Two of these LED's D2, D4 indicate the "COMM" and "INSERT/REMOVE" state of the comparator. D2 is lit when the comparator is in its "INSERT/REMOVE" mode and current to D2 is limited by resistor R11. LED D4 is lit when the comparator 10 is in a "COMM mode", with current to D4 being limited by resistor R13.

A third LED D3 is used to monitor the activity monitor operation and indicate the passage of serial-port data from the activity monitor to the host computer 30. The serial data line coming from the activity monitor 100 is sent to the non-inverting input of op-amp U4B. The inverting input of this op-amp U4B comes from voltage divider 69 and is a constant 0.6 volts. Op-amp U4B functions as a comparator so that when the serial data line is in a resting state (encountering from between +3 to +5 volts,) D3 is off. When the serial data line pulse is low as a character is transmitted, D3 will flash on. Current to D3 is limited by resistor R12.

The last LED which indicates the monitoring of the signal supply to the electromagnetic is more complicated in nature. LED D16 permits monitoring of the signal supply to the electromagnet L1 so that a direct visual comparison of the signal monitor 100 in detecting can be compared to the signal generated by the comparator 10. The activity monitor typically transmits a "-" character through its serial data port when detecting a signal and also transmits a "T" character through its port once every second, which serves as a time indicator. When the time indicator is turned off and the activity monitor no longer transmits "T" characters, the monitor transmits a character only when it has detected an event that is programmed to count. The monitor can count either zero-crossing events when it is placed in a "zero-crossing mode" (ZCM) or it can count the number of times the signal rises above zero when it is in a time-above-threshold (TAT) mode. The activity monitor is intended to be placed in its ZCM mode for comparator testing, wherein a character is transmitted every zero crossing and the time count characters are not transmitted. Typically, an interface will have an LED which will flash once a second when the "T" character is transmitted and will flash additionally when any countable events are detected.

The comparator will flash a signal in monitoring LED D16 when a zero-crossing occurs. Whenever the signal applied by the comparator 10 to its electromagnet L1 crosses a threshold, going either upward or downward, a brief flash of D16 results. If the monitor 100 is in a ZCM mode with the display of "T" characters turned off, the monitoring LED D16 should flash in synchronization with the activity monitor's serial data monitoring LED D3. It has been noted that this does not always occur in practice because of a phase shift in the activity monitor analog filters and some timing uncertainties associated with the monitors digital sampling. Monitoring LED D16 does indicate what the comparator signal generating circuit is doing. The comparator monitoring circuit described above receives a copy of the signal sent to the electromagnet L1 by way of resistor R52. The signal is applied to the inverting input of op-amp U18C, which serves as a voltage comparator with small hysteresis. Such hysteresis is supplied by R53. The reference voltage for comparator U18C comes from a voltage divider 70 which includes resistors R55, R56 and a potentiometer R54. R54 is adjusted to set the threshold set near the DC level of the magnet drive circuit. The divider 70 is connected to a source of regulated 2.5 volts which is applied to U18C through R51.

The signal from U18C passes through R57 and D1 into R58. D1 acts to prevent reverse voltage to U19, which is a dual monostable package such as a MM74HC4538 available from National Semiconductor. Both monostable units in the package U19 have the same time constant, which is set by RC networks R59 and C38, R60 and C39. One monostable of the package U19 is configured to trigger on a rising edge, while the other is set to trigger from a falling edge. The outputs of these two units are combined by diodes D14 and D15. The signal passes through R61, a current-limiting resistor for LED D16.

If the monitor 100 has an internal analog switch chip to switch the monitor output pin "BATT/RESET/ANO" between the monitor microcontroller reset line and analog signal output, the analog signal which the monitor 100 sees may be observed on the comparator LCD panel 28. The signal output of the monitor has a DC voltage of about 1.2 volts. In order to avoid use of a bipolar power supply, the monitor's analog circuits operate around a DC bias between the circuit ground and the battery +3 v voltage. A virtual ground is used in the monitor and is visible on the comparator panel meter 28. The panel meter is slow in updating readings because of a slow sampling rate and a DC offset.

The comparator 10 includes an improved means to observe the monitor's analog output. The analog signal from the monitor's "BATT/RESET/ANO" pin is filtered through an active low-pass filter circuit which includes resistors R46, R47, capacitors C14 and C17 and op-amp U18A. This signal is then brought to the non-inverting input of op-amp U18B through the voltage divider formed by R42 and R44 which divides the analog signal in half. The gain of op-amp U18B is two and therefore, the path gain from the monitor to output is unity.

Two resistors R41 and R43 set the non-inverting gain of op-amp U18B at two and the inverting gain at one. Voltage divider R38, R40 and potentiometer R39 produce a voltage of about 1.2 volts, which is subtracted from the monitor's analog signal by op-amp U18B. This offset voltage may be adjusted by the potentiometer R39. A capacitor C18 reduces noise on this DC offset signal, and the analog output is passed through R45 to protect against overload. Capacitor C16 may be provided for additional extra high-frequency noise filtering. Pins J4-13 and J4-14 carry the analog signal off the comparator circuit board 40 where it may be read by an auxiliary instrument, such as an oscilloscope.

Power is provided to the comparator 10 by way of a 12 volt DC adapter, or it may be powered by a switching power supply. The DC voltage is provided at pins J4-7 and J4-8 and passes through a fuse F1, after which it passes through a diode bridge 74 containing four diodes D5 through D8. A zener diode may also be provided to guard against voltage transients and a filter, such as capacitor C8 may also be provided. This provides the source for all 12 volt power to certain circuits, such as the DAC 34, transistor Q1, the op-amp packages U4, U16 and U18 as well as a voltage inverter U6 and regulator U7.

The power supply may also include a voltage inverter U6 which uses two capacitors C9 and C10 to develop a −12 volt supply for a +12 volt supply. Two other circuits develop the 5 volt power supply for the comparator 10. A voltage divider formed by R49 and R50 develops a −5 volt power supply, while voltage regulator U7 is used to produce a +5.6 volt power supply. The output of the regulator U7 is filtered by C7 on the low end and by C11 on the high end. The +5.6 volt value of this supply is necessary to compensate for a drop incurred by an input steering diode.

A bandgap voltage reference U17 is provided and powered through R17 to develop a 2.5 volt power source, which is buffered by U16C, a unity-gain voltage follower, and the output of which is the source for all circuit points designated "VREF". It also supplies buffer op-amp U16D which has an output, after inverting gain, of −5 volts, and which is the source for designated "VREF".

Figure 2:
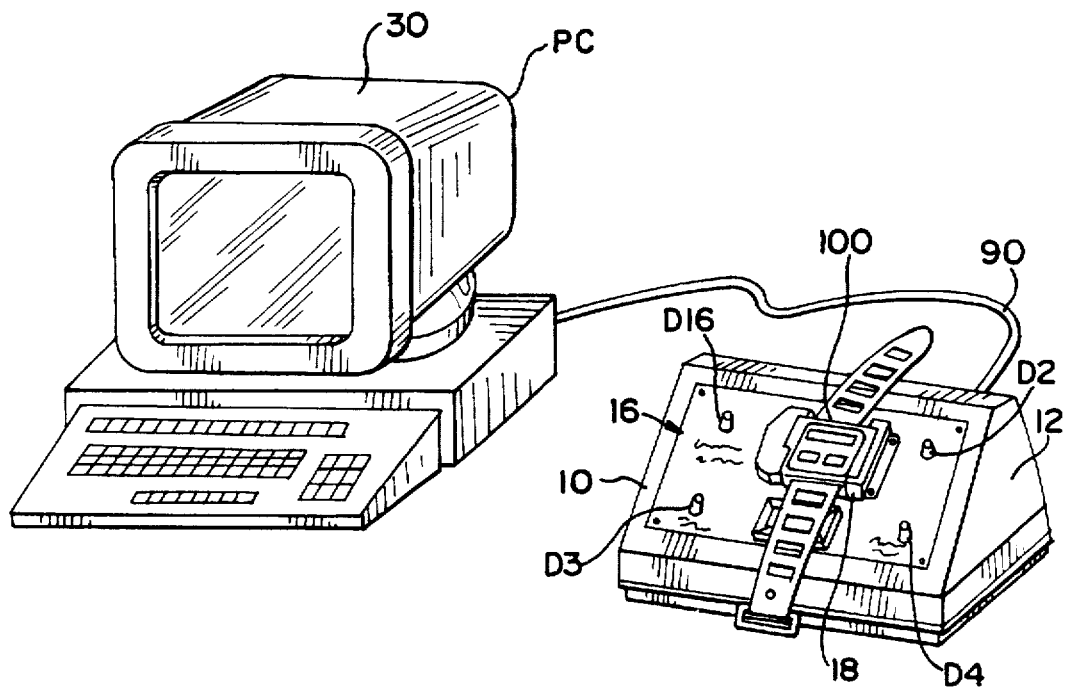
FIG. 2 is an activity monitor comparator system including a computer, an activity monitor and an activity monitor comparator constructed in accordance with the principles of the present invention.

In operation, an activity monitor 100 is inserted into the test fixture 17 of the comparator 10 as illustrated in FIG. 2 and the comparator is connected to a host computer 30 by way of a communication cable 80 extending between the serial data port of the computer (not shown) and the RS-232 connector of the comparator 10, typically located in the rear of the comparator housing 12.

A predetermined activity pattern is stored in the comparator ROM 32 in a digital format. This activity pattern may range from a predetermined activity test pattern to an actual pattern of human activity retrieved from an activity monitor. The former activity pattern may be suitable for calibration of monitors, while the latter activity pattern may be suitable for a determination of the accuracy or reliability of the monitors. A number of different ROMS, each containing different activity patterns, may be provided to the testing facility.

The digital activity pattern is thereupon converted into an analog signal by the DAC 34 which is supplied to the comparator excitation means, namely electromagnet 38. The electromagnet may then be pulsed at very low frequencies which replicate low frequencies associated with certain human activity, such as heart rates and respiration rates. These pulses influence the sensor 116 of the monitor and excite it, so that the monitor then records the activity. The activity so recorded is transferred to the computer 30 by way of an interface and the computer compares the recorded activity with the testing activity pattern.

Figure 8:
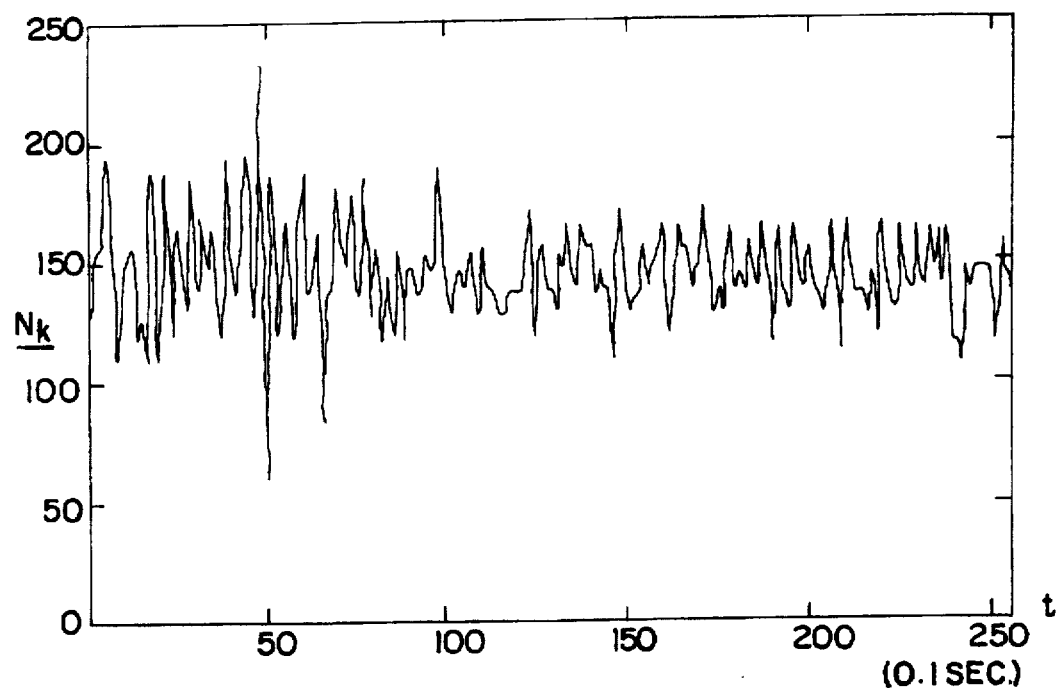
FIG. 8 is an amplitude vs. time plot of the patterns of activity recorded by an activity monitor worn on the wrist of a human subject; and, FIG. 9 is an amplitude vs. time plot of the patterns of activity rerecorded by a second activity monitor after excitation by the comparator electromagnet as driven by a DAC-produced analog waveform which was obtained from the digitized and ROM-stored waveform of FIG. 8.

FIG. 8 is a plot of an analog waveform pattern of activity which was constructed from actual binary data recorded by an activity monitor of the type described in the aforementioned '489 patent and strapped to the wrist of a human. This plot was created by converting digital data obtained from the activity monitor internal RAM to analog form by conversion software at a rate of 10 samples per second. The vertical axis of the plot is retrieved from an activity monitor RAM and is proportional to true acceleration. It represents the number of counts, $N_k$, recorded by the activity monitor sensor as converted from the voltage output of the monitor's internal sensor. The horizontal axis displays time in tenths of second such that a human activity pattern of a 25 second time length is illustrated. The data in FIG. 8 crosses a datum at about 150 counts, which represents the DC offset used by activity monitors described in the aforementioned '489 patent which permits the activity monitor to record both positive and negative acceleration.

Figure 9:
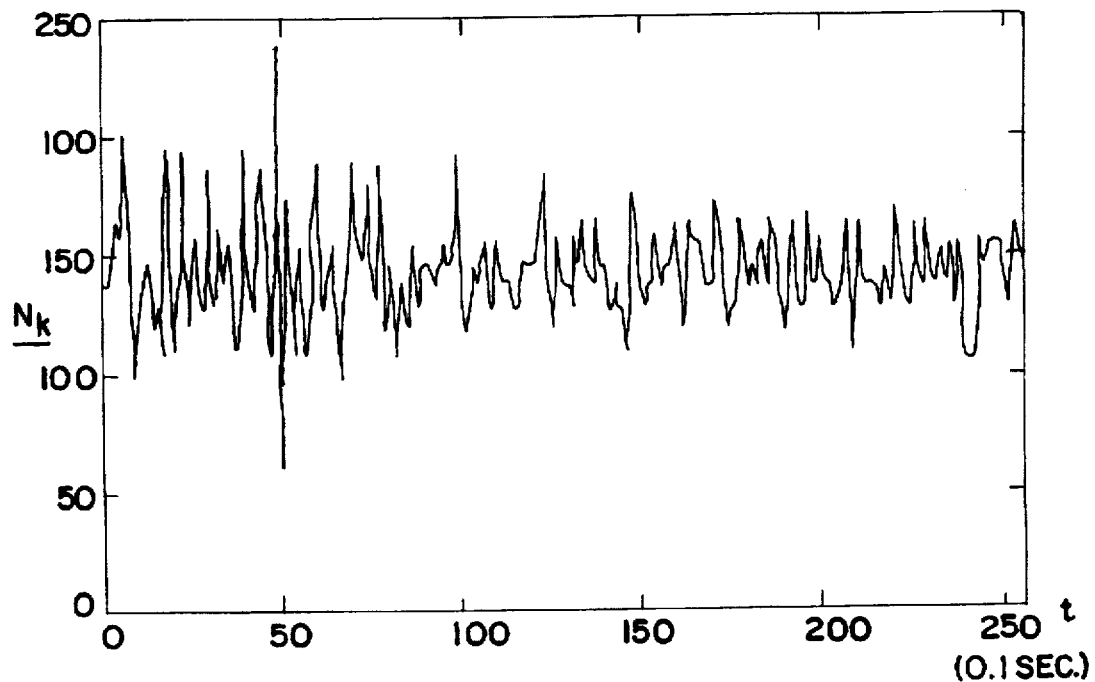

The waveform of FIG. 8 was redigitized and stored in binary format in a ROM playback chip 32. When inserted into a comparator and the data contained therein is clocked out, the DAC 34 converts the RAM playback data to a continuous realtime voltage waveform that substantially replicates the original waveform which is used to drive power transistor 36 which in turn drives electromagnet 38. When an activity monitor was placed in a comparator test fixture 17 and electromagnetically excited in accordance with the waveform of FIG. 8, the amplitude vs. time plot of FIG. 9 was obtained. The excitation of the electromagnet causes the activity monitor proof mass 118 to move in nearly complete synchronization with it. Because the waveform frequencies used are less than 20 Hz virtually no magnetic indication occurs to distort the testing the waveforms of FIG. 8 and 9 are virtually identical, thereby confirming the reproducability of the comparator signal generating circuitry.

While the preferred embodiment of the invention have been shown and described, it will be understood by those skilled in the art that changes or modifications may be made thereto without departing from the true spirit and scope of the invention.

We claim:

1. An activity monitor interface apparatus for providing an interface for data communication between an activity monitor having an internal sensor which determines activity of a subject using said activity monitor and a computer, the apparatus being capable of testing operation of the internal sensor of said activity monitor, said apparatus comprising:

a test platform;

test receptacle means for receiving an activity monitor and holding it substantially motionless upon the test platform in a testing position;

memory means for storing at least one predetermined test pattern of activity;

conversion means for converting the activity test pattern, upon retrieval from the memory means, into an excitation signal representative of said predetermined activity test pattern;

activity monitor exciting means which receives the excitation signal and applies an excitation force to an activity monitor held in said receptacle means in order to excite the activity monitor internal sensor in a manner which substantially replicates said predetermined activity test pattern; and data transmission means for transmitting data generated by said activity monitor held in said receptacle means in response to said excitation force for comparison with said predetermined activity test pattern.

2. The activity monitor interface apparatus as defined in claim 1, wherein said memory means includes a read-only memory (ROM) and said conversion means includes a digital-to-analog connector (DAC).

3. The activity monitor interface apparatus as defined in claim 2, wherein said activity monitor exciting means includes an electromagnet which generates a magnetic field upon application of said excitation signal, the magnetic field inducing a response in said activity monitor internal sensor.

4. The activity monitor interface apparatus as defined in claim 1, wherein said data transmission means includes a transformer and opto-isolated RS-232 communication datalink.

5. The activity monitor interface apparatus as defined in claim 1, wherein said test platform includes a housing, said test receptacle means being disposed on a surface of the housing, and said activity monitor exciting means includes an electromagnet disposed within said housing proximate to and opposing said test receptacle means.

6. The activity monitor interface apparatus as defined in claim 1, wherein said test pattern of activity has a frequency of between 0.2 and 10 Hz.

7. The activity monitor interface apparatus as defined in claim 1, further including an RS-232 data port for transmitting said data generated by said activity monitor.

8. An activity monitor interface apparatus for providing an interface for data communication between an activity monitor and a computer for testing the activity monitor, the activity monitor having a sensor which determines activity of a subject using said monitor and which generates an output indicative of the activity of said subject, the interface apparatus comprising:

test receptacle means for receiving an activity monitor and holding it substantially motionless upon the test platform in a testing position;

activity monitor exciting means which receives a predetermined excitation signal and applies an excitation force in response to receipt of said predetermined excitation signal, the activity monitor exciting means applying said excitation force to an activity monitor held in said receptacle means in order to excite the activity monitor; and data transmission means for transmitting data generated by said activity monitor held in said receptacle means in response to said excitation force for comparison with said predetermined excitation signal.

9. The activity monitor interface apparatus as defined in claim 8, further including memory means for storing in digital format at least one predetermined test pattern of activity and conversion means for converting the predetermined test pattern into said predetermined excitation signal.

10. The activity monitor interface apparatus as defined in claim 9, wherein said conversion means includes a digital-to-analog convertor (DAC) which converts said predetermined test pattern into said predetermined excitation signal.

11. The activity monitor interface apparatus as defined in claim 10, further including driving means for driving said activity monitor exciting means in response to said predetermined excitation signal, the driving means receiving said predetermined excitation signal from said conversion means in the form of a voltage output from said DAC.

12. The activity monitor interface apparatus as defined in claim 11, wherein said driving means includes a transistor and said activity monitor exciting means includes an electromagnet driven by said transistor, said transistor receiving a voltage output from said conversion means as said predetermined excitation signal and said driving means outputting said predetermined excitation signal as a current to said electromagnet to thereby generate said excitation force in the form of a magnetic field which replicates said predetermined test pattern of activity.

13. The activity monitor interface apparatus as defined in claim 9, wherein said memory means includes a ROM.

14. An apparatus for testing an activity monitor to determine at least one operational characteristic of the activity monitor, said activity monitor including an activity sensor which is responsive to an applied magnetic field, the apparatus comprising means for applying a magnetic field to said activity monitor sensor to test said activity monitor sensor and means for determining the responsiveness of said activity monitor sensor to the applied magnetic field, said magnetic field being variable in order to excite said activity monitor sensor in accordance with a variety of predetermined test patterns.

15. A system for assessing operation of an activity monitor, comprising:

means for storing a predetermined test pattern of activity in memory, conversion means for converting the predetermined test pattern of activity to a voltage and outputting the voltage as an excitation signal which substantially replicates said predetermined test pattern of activity, generating means for generating a current in synchronization with said voltage output from said conversion means and outputting said current, a receptacle for receiving an activity monitor and holding it motionless during assessment of the operation of the activity monitor, means for generating a magnetic field proximate to said receptacle in response to said current output by the current generating means in accordance with said predetermined test pattern of activity, which induces a response in said activity monitor when received within said receptacle, and a computer for correlating said predetermined test pattern of activity to said activity monitor response and determining any differences therebetween.

16. The system as defined in claim 15, wherein said means for storing includes a read-only-memory.

17. The system as defined in claim 15, wherein said conversion means for converting includes a digital-to-analog converter.

18. The system as defined in claim 15, wherein said generating means for generating includes a transistor.

19. The system as defined in claim 15 further comprising response signal generating means for generating a response signal resulting from said response of said activity monitor and data transmission means for transmitting said response signal to said computer.

20. An activity monitor interface apparatus for interfacing between a processing unit and an activity monitor and for testing operation of the activity monitor, said activity monitor being one which is worn by a subject and detects and records occurrences of body movements of the subject, the interface apparatus comprising:

a receptacle unit which receives said activity monitor during testing of said activity monitor;

an excitation component that applies an excitation signal of interest to said activity monitor received in said receptacle during testing of said activity monitor to induce said activity monitor to generate a response signal in response to said excitation signal; and, a transmission path that provides an electrical communication path between said receptacle unit and a processing unit, the transmission path transmitting the response signal generated by said activity monitor to the processing unit for comparison with said excitation signal.

* * * * *